(12) United States Patent
Samchukov et al.

(10) Patent No.: US 9,445,841 B2
(45) Date of Patent: Sep. 20, 2016

(54) WIRE TENSIONER TIP FOR USE WITH WIRE FIXATION BOLT

(71) Applicant: TEXAS SCOTTISH RITE HOSPITAL FOR CHILDREN, Dallas, TX (US)

(72) Inventors: Mikhail L. Samchukov, Coppell, TX (US); John David Ross, Ovilla, TX (US); Alexander M. Cherkashin, Flower Mound, TX (US); John G. Birch, Dallas, TX (US)

(73) Assignee: TEXAS SCOTTISH RITE HOSPITAL FOR CHILDREN, Dallas, TX (US)

( * ) Notice: Subject to any disclaimer, the term of this patent is extended or adjusted under 35 U.S.C. 154(b) by 2 days.

(21) Appl. No.: 14/565,936

(22) Filed: Dec. 10, 2014

(65) Prior Publication Data
US 2016/0166285 A1 Jun. 16, 2016

(51) Int. Cl.
*A61B 17/62* (2006.01)
*A61B 17/66* (2006.01)
A61B 17/56 (2006.01)

(52) U.S. Cl.
CPC .............. *A61B 17/66* (2013.01); *A61B 17/62* (2013.01); *A61B 2017/564* (2013.01)

(58) Field of Classification Search
CPC . A61B 17/62; A61B 17/66; A61B 2017/564
USPC .................. 606/54, 56, 57, 58, 59, 103, 105
See application file for complete search history.

(56) References Cited

U.S. PATENT DOCUMENTS

| | | |
|---|---|---|
| 1,257,297 A | 2/1918 | Brown |
| 2,250,417 A | 7/1941 | Ettinger |
| 2,346,346 A | 4/1944 | Anderson |
| 4,392,487 A | 7/1983 | Selner et al. |
| 4,708,131 A | 11/1987 | Kendrick |
| 4,865,023 A | 9/1989 | Craythorne et al. |
| 4,955,370 A | 9/1990 | Pettine |
| 5,407,420 A | 4/1995 | Bastyr et al. |
| 5,429,637 A | 7/1995 | Hardy |
| 5,431,659 A | 7/1995 | Ross, Jr. et al. |
| 5,451,225 A | 9/1995 | Ross, Jr. et al. |
| 5,702,389 A | 12/1997 | Taylor et al. |

(Continued)

OTHER PUBLICATIONS

International Search Report and Written Opinion, PCT/US2015/064956, dated Mar. 4, 2016, 12 pages.

*Primary Examiner* — Pedro Philogene
*Assistant Examiner* — David C Comstock
(74) *Attorney, Agent, or Firm* — Baker & McKenzie LLP (57) ABSTRACT

A wire tensioner tip for use with a wire fixation bolt. First and second wires may be anchored to and tensioned across an external fixator frame with first and second wire tensioners. The first and second wires may be anchored at first anchor locations with first and second wire fixation bolts. First and second wire tensioner tips may engage with third and fourth wire fixation bolts, thereby preventing the third and fourth wire fixation bolts from rotating. The first and second wires may be tensioned to a desired tension with the first and second wire tensioners at the same time to prevent over-tensioning or under-tensioning. The first and second wires may be anchored at second anchor locations with third and fourth wire fixation bolts. By engaging the wire fixator bolts with the wire tensioning tips, fewer tools are required and one medical professional can tension two wires at once.

29 Claims, 10 Drawing Sheets

(56) References Cited

U.S. PATENT DOCUMENTS

| | | | |
|---|---|---|---|
| 5,728,095 A | 3/1998 | Taylor et al. | |
| 5,931,837 A | 8/1999 | Marsh et al. | |
| 6,461,358 B1 | 10/2002 | Faccioli et al. | |
| 7,044,926 B2 | 5/2006 | Carlson | |
| 7,182,743 B2 | 2/2007 | Slautterback et al. | |
| 7,306,601 B2 | 12/2007 | McGrath et al. | |
| 7,507,215 B2 | 3/2009 | Ryan | |
| 7,931,650 B2 | 4/2011 | Winquist et al. | |
| 8,382,755 B2 | 2/2013 | Austin et al. | |
| 8,608,740 B2 * | 12/2013 | Butikofer | A61B 17/6458 606/59 |
| 8,679,117 B2 | 3/2014 | Knuchel et al. | |
| 8,727,972 B2 | 5/2014 | Zhang et al. | |
| 2006/0287652 A1 | 12/2006 | Lessig et al. | |
| 2010/0298827 A1 | 11/2010 | Cremer et al. | |
| 2012/0184958 A1 * | 7/2012 | Knuchel | A61B 17/62 606/59 |

\* cited by examiner

WIRE TENSIONER TIP FOR USE WITH WIRE FIXATION BOLT

TECHNICAL FIELD

The present disclosure relates to a wire tensioner for use with an external fixator frame, wires, and wire fixation bolts, and more particularly, to an improved wire tensioner tip for engaging directly with a wire fixation bolt.

BACKGROUND

External orthopedic fixation devices are commonly used in the treatment of limb injuries and deformations including skeletal fractures, soft tissue injuries, delayed union of skeletal bones resulting from slow healing, non-union of skeletal bones involving unhealed bones, mal-union of bones resulting from the improper healing of broken or fractured bones, congenital deformities resulting from bones developing in a mal-position, and bone widening or twisting. Medical procedures involving external orthopedic fixation devices include limb lengthening, deformity correction, and the treatment of fractures, mal-unions, non-unions, and bone defects. Typically, external fixator systems may be placed on a subject's (e.g., a human or another vertebrate animal) affected limb by a surgeon to set the impacted bones or bone fragments in a desired position. The fixator systems may be adjusted throughout the treatment process in order to set and maintain the bones in a desired position.

External fixator systems often comprise fixation rings, threaded rods or struts, and wires or pins. The subject's affected limb may be received within the fixation rings and the threaded rods or struts may be used to control the distance and angles of the fixation rings relative to each other. The wires or pins may extend across the fixation rings through the subject's affected limb (e.g., through the bone and/or soft tissue), and the wires or pins may be connected to the fixation rings with nuts and bolts. However, before the wire may be fixed across the fixation rings by the nuts and bolts, the wire must be tensioned to an optimal tension, which is a difficult, complicated, and overly wieldy procedure.

Known tensioning methods require multiple steps, and often more than one person, to properly tension wires across the fixation rings. First, a first end of the wire is fixed with a nut and a bolt to a first connection point on the fixation ring. One or more wrenches must be used to tighten the nut and the bolt at the first connection point before the wire may be tensioned. Next, the wire is stretched across the fixation ring and must be tensioned while a second end of the wire is fixed with a nut and a bolt to a second connection point on the fixation ring. In addition to the one or more wrenches that must be used to tighten the nut and the bolt at the first connection point, a tensioner must be used to tension the wire. As such, three instruments—a first wrench to tighten the nut, a second wrench to provide counter-torque on the bolt, and at least one tensioner to tension the wire—must be used at the same time, therefore requiring more than one person to tension the wire across the fixation ring.

In addition, known wire tensioning methods tension the wire against the fixation ring. If the wires are not oriented orthogonally to the outer surface of the fixation ring, the tensioner may slip under heavy loads, preventing the wires from being properly tensioned and possibly injuring the surgeon, the patient, or both.

Therefore, it is desirable to have an improved wire tensioner tip that is operable to engage with a wire fixation bolt and that is operable to be manipulated by one person to tension and secure a wire across an external fixation frame.

BRIEF SUMMARY

Disclosed herein is an improved wire tensioner tip for use with wire fixation bolts. The wire fixation system may comprise an external fixator frame comprising an upper surface and a lower surface and a plurality of bolt apertures extending from an upper surface to a lower surface. One or more wires may be operable to be extended across the external fixator frame and through a bony structure of a subject's limb. The wire fixation system may further comprise at least first and second wire fixation bolts received through bolt apertures of the external fixator frame. Each wire fixation bolt may comprise a head portion and a threaded shaft portion extending along an axis. The head portion of each wire fixation bolt may comprise a shaped head, a first body distal to the shaped head, a shoulder distal to the first body, and a second body distal to the shoulder. The head portion of each wire fixation bolt may further comprise a wire aperture extending perpendicularly to the axis of the wire fixation bolt and through the second body and an offset wire groove extending perpendicularly to the axis of the wire fixation bolt and partially through a distal surface of the shoulder and partially though a proximal portion of the second body.

The wire fixation system may further comprise at least first and second nuts operable to be threaded onto the threaded shaft portions of the first and second wire fixation bolts. Each nut may be configured to bias the head portion of the wire fixation bolts against the upper surface of the external fixator frame.

The wire fixation system may further comprise a wire tensioning tip operable to engage with the second wire fixation bolt and with a wire tensioning device. The wire tensioning tip may further comprise a shaped head recess portion operable to engage with the shaped head of the wire fixation bolt, a body shoulder portion distal to the shaped head recess portion and operable to engage with the first body of the wire fixation bolt, and a shoulder recess portion distal to the body shoulder portion and operable to engage with the shoulder of the wire fixation bolt. The wire tensioning tip is operable to stabilize the head portion of the second wire fixation bolt and prevent the second wire fixation bolt from rotating when the wire tensioning tip is received onto the wire and engaged with the shaped head of the second wire fixation bolt.

A wire fixation bolt comprising: a head portion, wherein the head portion further comprises: a shaped head; a first body distal to the shaped head; a shoulder distal to the first body; a second body distal to the shoulder; a wire aperture extending perpendicularly to the axis of the wire fixation bolt and through the second body; and an offset wire groove extending perpendicularly to the axis of the wire fixation bolt and partially through a distal surface of the shoulder and partially though a proximal portion of the second body; and a threaded shaft portion.

BRIEF DESCRIPTION OF THE DRAWINGS

Embodiments are illustrated by way of example in the accompanying figures, in which like reference numbers indicate similar parts, and in which.

DETAILED DESCRIPTION

In the embodiments described below, various components may be defined in relation to each other using the positional terms of superior/inferior, medial/lateral, and distal/proximal. In operation and while used during surgery, "proximal" refers to closer to the user/surgeon, while "distal" refers to away from the user/surgeon and closer to the subject/patient.

Figure 1:
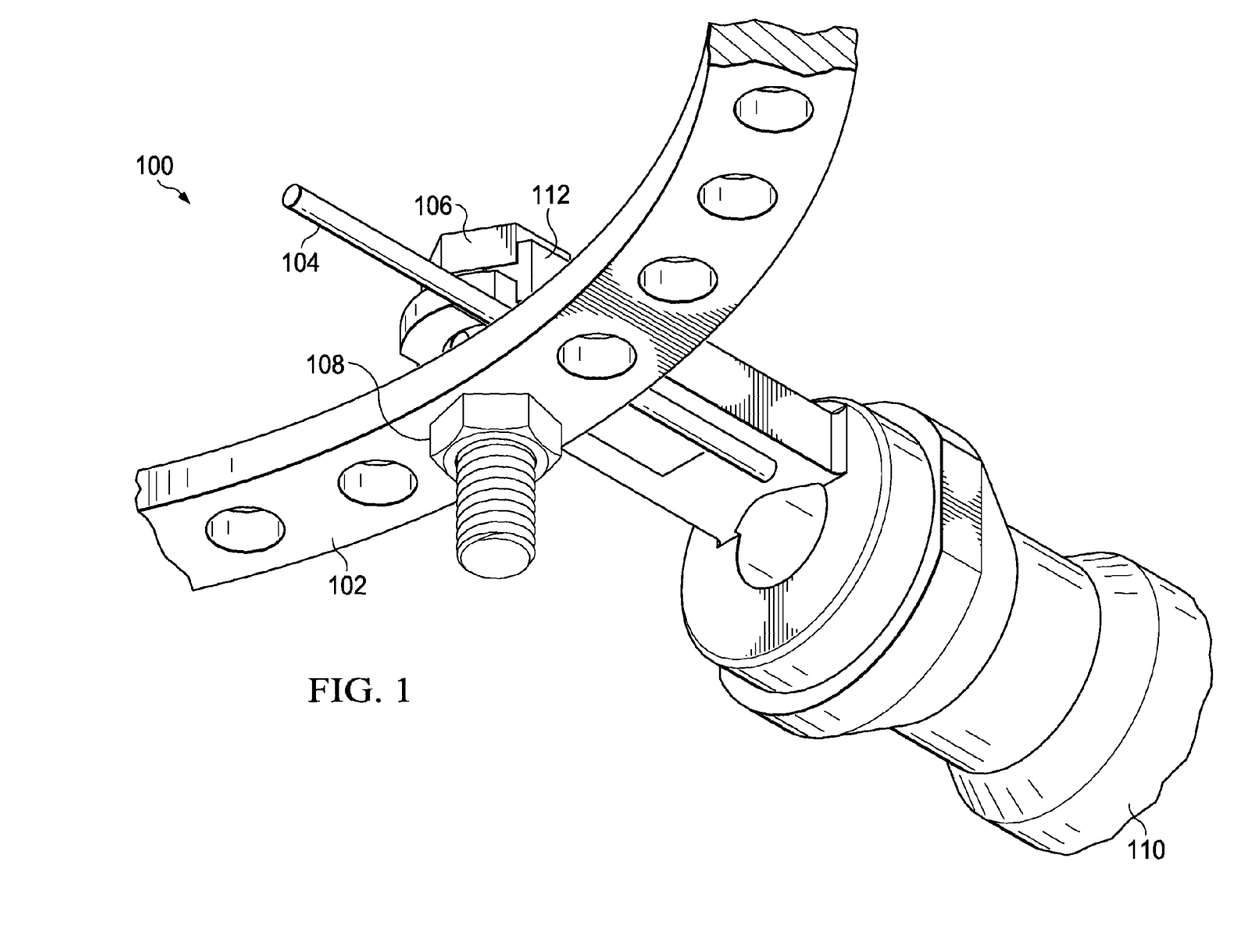
FIG. 1 illustrates a bottom elevational view of a wire fixation system, in accordance with one embodiment of the present disclosure.

FIG. 1 illustrates a bottom elevational view of a wire fixation system 100, in accordance with one embodiment of the present disclosure. The wire fixation system 100 comprises an external fixator frame 102, a wire 104, a wire fixation bolt 106, a nut 108, and a wire tensioner 110 comprising a wire fixation tip 112. In the disclosed embodiments, the wire 104 may be tensioned against the wire fixation bolt 106 and only two tools—the wire tensioner 110 and a wrench (not shown)—may be needed to tension and secure the wire 104 relative to the external fixator frame 102. Each individual component is described below in more detail.

Figure 2:
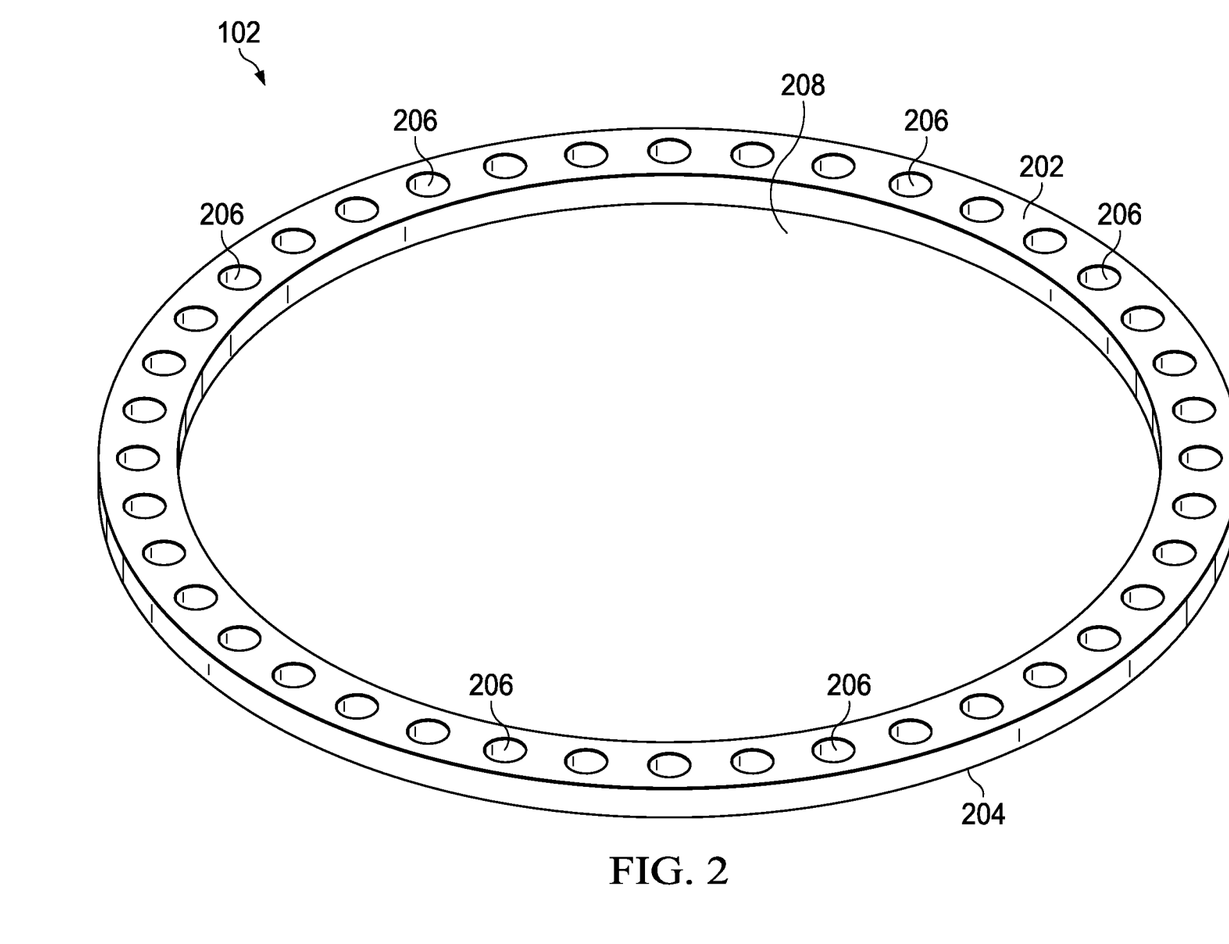
FIG. 2 illustrates an elevational view of the external fixator frame of FIG. 1, in accordance with one embodiment of the present disclosure.

FIG. 2 illustrates an elevational view of the external fixator frame 102 of FIG. 1, in accordance with one embodiment of the present disclosure. As depicted in FIG. 1, the external fixator frame 102 may be a circular fixator frame, although in other embodiments, the external fixator frame 102 may be oval-shaped, square-shaped, rectangular-shaped, or any other regular or irregular shape configured for an external fixation application. The external fixator frame 102 may comprise an upper surface 202, a lower surface 204, and a plurality of bolt apertures 206 extending from the upper surface 202 to the lower surface 204. The external fixator frame 102 may further comprise a central aperture 208 that is operable to receive one or more bony structures (not shown) therethrough.

Figure 3:
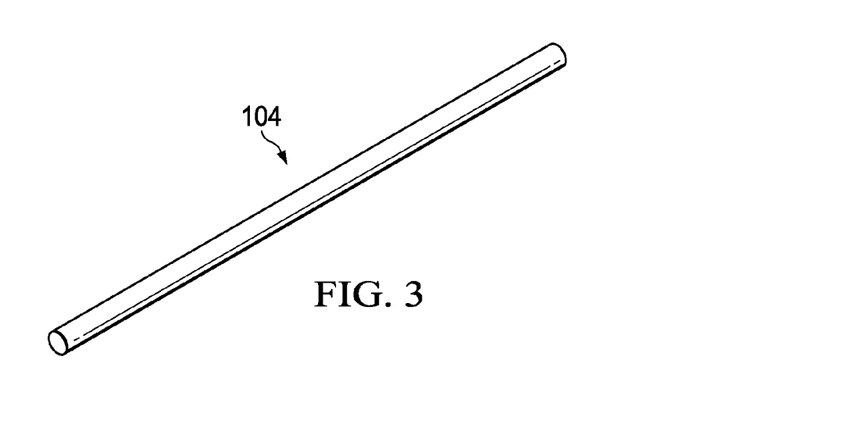
FIG. 3 illustrates an elevational view of the wire of FIG. 1, in accordance with one embodiment of the present disclosure.

FIG. 3 illustrates an elevational view of the wire 104 of FIG. 1, in accordance with one embodiment of the present disclosure. In an embodiment, the wire 104 is operable to be tensioned between two external fixation bolts across the external fixator frame of FIG. 2. In a preferred embodiment, the wire 104 may be operable to be tensioned to approximately 130 kilograms across the external fixator frame, although in other embodiments, the wire 104 may be operable to be tensioned to approximately 100 kilograms to approximately 160 kilograms across the external fixator frame. In an embodiment, the wire 104 may comprise a diameter of 1.8 mm, although in other embodiments, the wire may comprise a diameter of between approximately 1.5 mm to approximately 2.0 mm.

Figure 4:
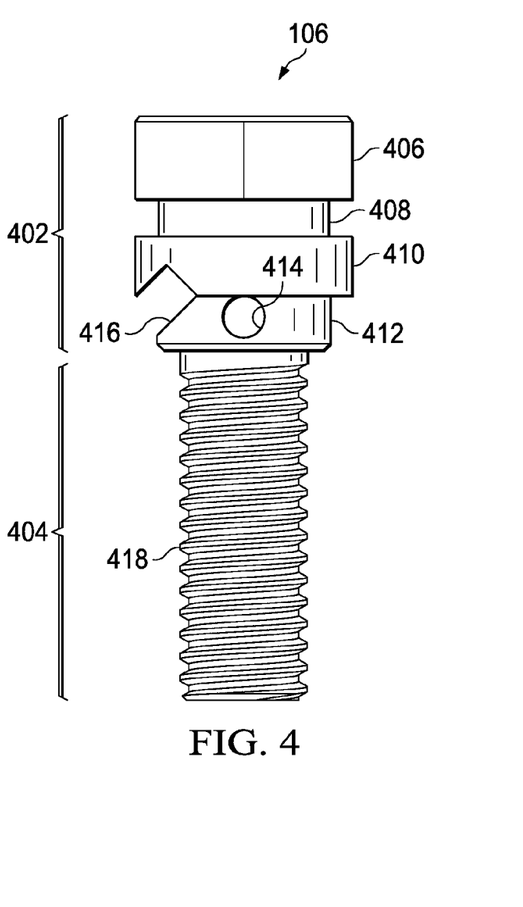
FIG. 4 illustrates a side elevational view of the wire fixation bolt of FIG. 1, in accordance with one embodiment of the present disclosure.

FIG. 4 illustrates a side elevational view of the wire fixation bolt 106 of FIG. 1, in accordance with one embodiment of the present disclosure. The wire fixation bolt 106 may comprise a head portion 402 and a threaded shaft portion 404 and a longitudinal axis extending along a length of the wire fixation bolt 106. Opposite the threaded shaft portion 404, the head portion 402 may comprise a shaped head 406. The shaped head 406 may be a hex-shaped head, although in other embodiments, the shaped head 406 may be a multi-faceted head or a rounded head with one or more flutes. The head portion 402 may further comprise a first body 408 distal to the shaped head 406, i.e. further from a surgeon's hand and closer to a subject's body. The first body 408 may be rounded, although it other embodiments, the first body 408 may be squared, hex-shaped, multi-faceted, or generally rounded with one or more straight edges. The head portion 402 may further comprise a shoulder 410 distal to the first body 408. The first body 408 may be generally rounded with one or more straight edges, although in other embodiments, the first body 408 may be squared, hex-shaped, rounded, or multi-faceted. The head portion 402 may further comprise a second body 412 distal to the shoulder 410 and proximate to the threaded shaft portion 404. The second body 412 may be rounded, although it other embodiments, the second body 412 may be squared, hex-shaped, multi-faceted, or generally rounded with one or more straight edges. In an embodiment, the shaped head 406 and the shoulder 410 may have a first, larger diameter while the first body 408 and the second body 412 may have a second, smaller diameter approximately the same or larger as a diameter of the threaded shaft portion 404.

The head portion 402 of the wire fixation bolt 106 may further comprise a wire aperture 414 extending perpendicularly to the longitudinal axis of the wire fixation bolt 106 depicted in this embodiment through the second body 412. The head portion 402 of the wire fixation bolt 106 may further comprise an offset wire groove 416 extending perpendicularly to the longitudinal axis of the wire fixation bolt 106 and in this embodiment depicted as extending partially through a distal surface of the shoulder 410 and partially through a proximal portion of the second body 412. The offset wire groove 416 may be offset to one side of the head portion 402 and offset from the longitudinal axis of the wire fixation bolt 106. Generally, the wire aperture 414 and offset wire groove 416 will be parallel, although in some embodiments they may be angled so as not to be parallel, e.g., they may be offset by 1, 2, 3, 4, 5, 6, 7, 8, 9, 10 or more degrees. Further, in other embodiments, the wire aperture 414 and offset wire groove 416 may be positioned to traverse other parts of the wire fixation bolt 106, e.g., one or more of the shaped head 406, shoulder 410, first body 408, second body 412, or cross into the threaded shaft portion 404. The shape of the wire fixation tip 112 can be adjusted accordingly. In another embodiment, the offset wire groove 416 may not be a groove, but another opening in the wire fixation bolt 106.

The offset wire groove 416 may comprise one or more perpendicular grooves (not shown) on the distal surface of the shoulder 410 operable to prevent the wire (not shown) from sliding within the offset wire groove 416 when the wire is received therewithin. In an embodiment, the wire fixation bolt 106 and the wire 104 may form a bi-metal interface wherein the wire fixation bolt 106 may be manufactured from a stainless steel alloy that is stronger than the stainless steel wire 104. The one or more perpendicular grooves may be operable to bite into the wire 104 in order to prevent wire slippage within the offset wire groove 416 when the wire 104 is tensioned. See the discussion related to the embodiment depicted in FIG. 9 of U.S. Pat. No. 5,451,225 to Ross et al., the entirety of which is hereby incorporated by reference.

As depicted in FIG. 4, the wire aperture 414 may be located distal to the offset wire groove 416 such that the offset wire groove 416 is closer to the shaped head 406 of the head portion 402 and the wire aperture 414 is closer to the threaded shaft portion 404 of the wire fixation bolt 106. However, the skilled artisan will recognize that other positions can be selected for the offset wire groove 416 and the wire aperture 414 as outlined hereinabove so long as they are generally perpendicular to the longitudinal axis of the wire fixation bolt 106.

The threaded shaft portion 404 of the wire fixation bolt 106 may extend distally from the head portion 402 and may comprise threads 418 operable to engage with the nut 108 of FIG. 1. In certain embodiments, the wire fixation bolt 106 may have more than one thread 418 such that a wire 104 in offset wire groove 416 can be secured independently from a wire 104 in the wire aperture 414.

Figure 5:
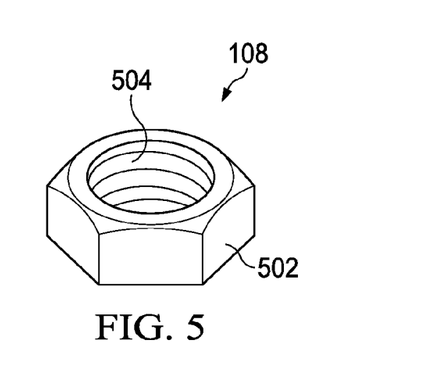
FIG. 5 illustrates an elevational view of the nut of FIG. 1, in accordance with one embodiment of the present disclosure.

FIG. 5 illustrates an elevational view of the nut 108 of FIG. 1, in accordance with one embodiment of the present disclosure. The nut 108 may comprise an outer hex shape 502 and an inner threaded aperture 504. The nut 108 may be operable to engage with the threaded shaft portion 404 of the wire fixation bolt 106 of FIG. 4. When a wire fixation bolt is received through a bolt aperture of the external fixator frame, the nut 108 is operable to bias the head portion of the wire fixation bolt against the upper surface of the external fixator frame, thereby tightening the wire fixation bolt against the external fixator frame.

Figure 6:
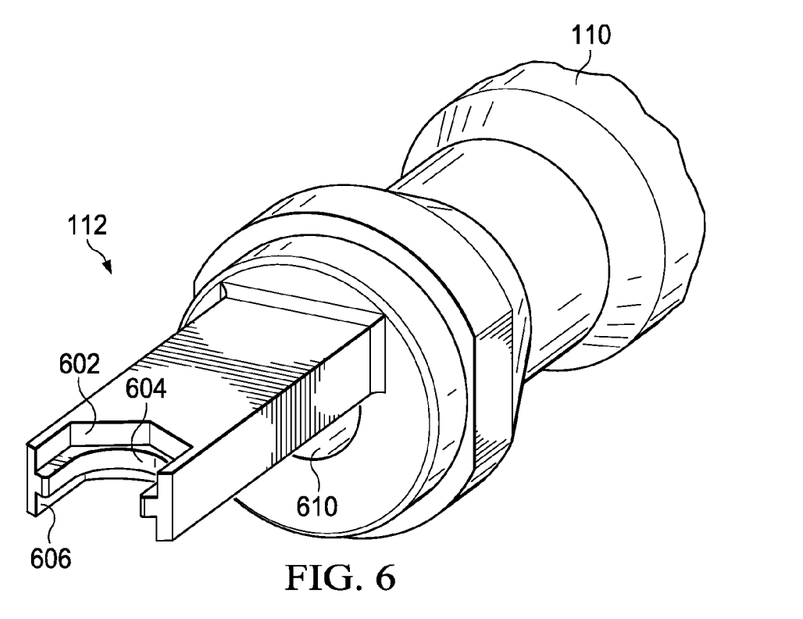
FIG. 6 illustrates a top elevational view of the wire tensioning tip of FIG. 1, in accordance with one embodiment of the present disclosure.
Figure 7:
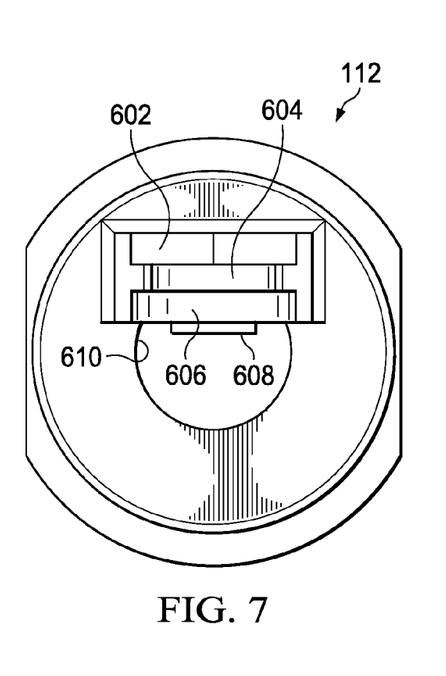
FIG. 7 illustrates an end view of the wire tensioning tip of FIG. 6, in accordance with one embodiment of the present disclosure.
Figure 8:
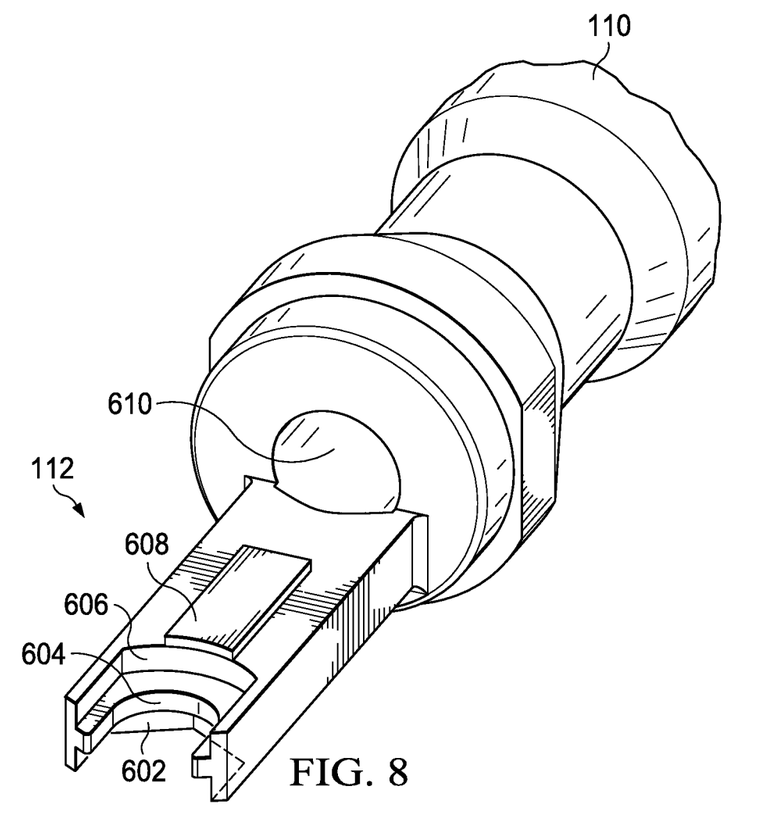
FIG. 8 illustrates a bottom elevational view of the wire tensioning tip of FIG. 6, in accordance with one embodiment of the present disclosure.

FIG. 6 illustrates a top elevational view of the wire tensioning tip 112 of FIG. 1, FIG. 7 illustrates an end view of the wire tensioning tip 112 of FIG. 6, and FIG. 8 illustrates a bottom elevational view of the wire tensioning tip 112 of FIG. 6, in accordance with one embodiment of the present disclosure. The wire tensioning tip 112 may be connected to and extend from any known wire tensioner 110, such as the Orthofix TrueLok® wire tensioner, as depicted and described in more detail in relation to FIG. 13. The wire tensioner 110 may be operated with one or two hands to tension the wire 104 across the external fixator frame. The wire tensioner 110 depicted in FIG. 13 uses a ratchet and clasping mechanism to incrementally move the wire 104 in a distal direction 1301 away from the patient, thus tightening the wire 104 for attachment to an external fixation frame. In use, a wire 104 is inserted into a body 1310 of the tensioner 110 such that the wire 104 is engaged by the clasping mechanism in to the body 1310 of the tensioner 110. By moving arms 1320 towards each other, the clasping mechanism incrementally moves the wire 104 in the distal direction 1301, thus causing the section of the wire 104 between the wire fixation bolts 106 and the external fixation frame 102 to become tensioned. A tension meter (not shown) may be incorporated into the wire tensioner 110 to accurately control the amount of tensioning force applied to the wire 104. The wire tensioner 110 may also include a ratchet release arm 1330 that can release the ratchet and clasping mechanism from the wire 104, thus allowing the wire tensioner 110 to be removed from the wire 104. The wire tensioning tip 112 extends from the wire tensioner 110 in order to prevent the wire tensioner 110 from contacting the external fixator frame of FIG. 1 while still allowing the wire tensioning tip 112 to slightly bend the wire of FIG. 1.

As depicted in FIGS. 6-8, the wire tensioning tip 112 comprises a shaped head recess portion 602 operable to engage with the shaped head 406 of the wire fixation bolt 106. The shaped head recess portion 602 may be a hex-shaped head, although in other embodiments, the shaped head recess portion 602 may be a multi-faceted head recess portion or a rounded head recess portion operable to engage with one or more flutes. The wire tensioning tip 112 may further comprise a body shoulder portion 604 distal to the shaped head recess portion 602, i.e. further from a surgeon's hand and closer to a subject's body, and operable to engage with the first body 408 of the wire fixation bolt 106. The body shoulder portion 604 may be rounded, although in other embodiments, the body shoulder portion 604 may be squared, hex-shaped, multi-faceted, or generally rounded with one or more straight edges. The wire tensioning tip 112 may further comprise a shoulder recess portion 606 distal to the body shoulder portion 604. The shoulder recess portion 606 may be generally rounded with one or more straight edges, although in other embodiments, the shoulder recess portion 606 may be squared, hex-shaped, rounded, or multi-faceted. The shoulder recess portion 606 should be operable to engage with the shoulder 410 of the wire fixation bolt 106. Accordingly, the surface of the shaped head recess portion 602, the body shoulder portion 604, and the shoulder recess portion 606 should mate with the surfaces of the shaped head 406, the first body 408, and the shoulder 410, respectively, to releasably connect the wire fixation bolt 106 to the wire tensioning tip 112. As depicted in FIGS. 6-8, the wire tensioning tip 112 may engage with four sides of a hex-shaped wire fixation bolt to releasably connect the wire fixation bolt 106 to the wire tensioning tip 112. Alternatively, the relative positions of the shaped head recess portion 602, body shoulder portion 604, and shoulder recess portion 606 may be reversed, such that the shaped head recess portion 602 and shoulder recess portion 606 are more distal from the surgeon's hand and closer to a subject's body.

Figure 13:
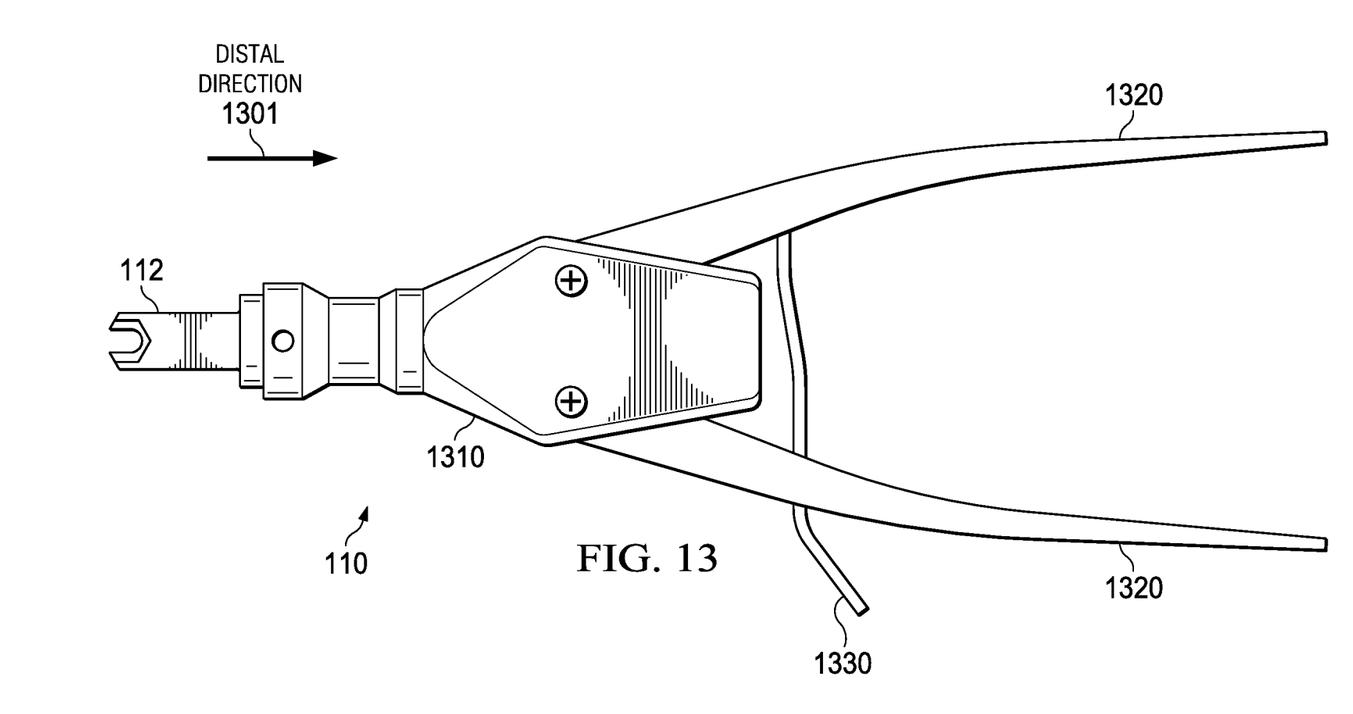
FIG. 13 illustrates a tensioner device with the wire tensioning tip of FIG. 1, in accordance with one embodiment of the present disclosure.

As depicted in FIGS. 7 and 8, the underside of the wire tensioning tip 112 may further comprise a boss 608. The boss 608 may be the same height as the difference in the height between the wire aperture 414 and the offset wire groove 416 of the head portion 402 of the wire fixation bolt 106 of FIG. 4, thus allowing the wire tensioning tip 112 to align with either the wire aperture 414 or the offset wire groove 416 when the wire tensioning tip 112 engages with the wire fixation bolt 106. The wire tensioning tip 112 further comprises an tensioning tip aperture 610 that is operable to receive and tension the wire 104 of FIG. 3. When the wire 104 is received within the tensioning tip aperture 610 of the wire tensioning tip 112, the wire tensioner 110 of FIG. 13 is operable to tension the wire 104 to a desired tension, as described in reference to FIG. 13.

In operation and during a surgical procedure, one or more wires may be surgically implanted into a subject's body through soft tissue and a bony structure, and an external fixator frame may be received or positioned around the subject's body proximate to the implanted wires. The wires may be connected to and tensioned across an external fixator frame in order to stabilize an injury or facilitate bone growth. The one or more wires may comprise a sharp tip that is inserted through the skin and soft tissue on an entry side until the one or more wires come in contact with a bony structure. The one or more wires may then be drilled under power through both cortexes of the bony structure and advanced manually by pushing or tapping the one or more wires through the soft tissue and skin until the one or more wires exit the limb on the opposite, exit side. The skin may be cut with a scalpel when the sharp end of the one or more wires begin to push out of the skin. The drill is then removed and one end of each of the one or more wires is anchored at a first end. A stopper, or olive, may be used to position the one or more wires in desired positions relative to the bony structure. The one or more wires may be advanced through the subject's limb until a stopper on each wire comes in contact with the first cortex of the bony structure on the entry side. By anchoring the stopper side first, when the surgeon tensions the wire on the exit side opposite the stopper, the stopper will not pull away from the bony structure and the stopper may be used to move the bony structure to a more-desired location within the external fixator frame.

Figure 9:
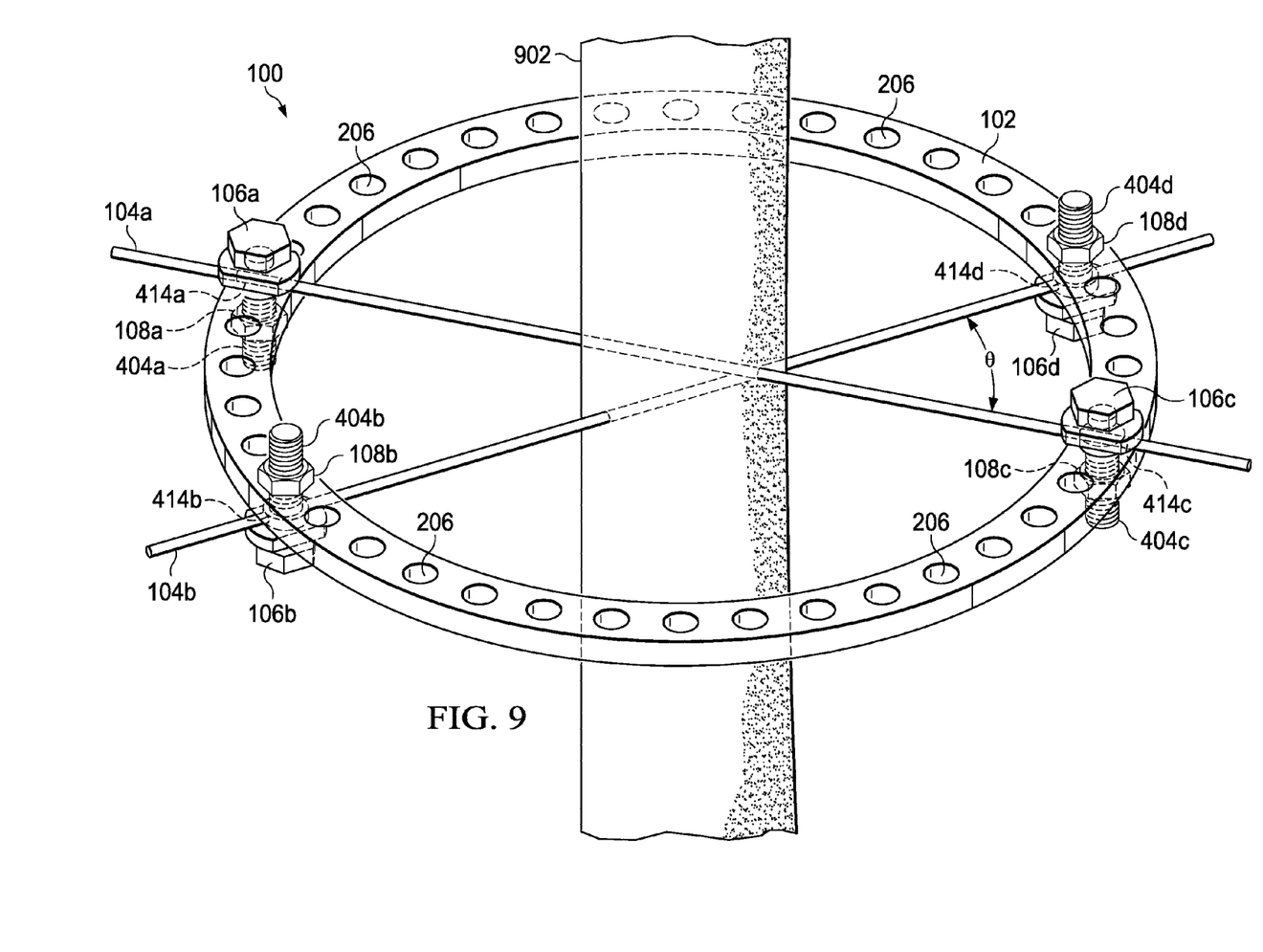
FIG. 9 illustrates an elevational view of the wire fixation system of FIG. 1 tensioned through a bony structure, in accordance with one embodiment of the present disclosure.

FIG. 9 illustrates an elevational view of the wire fixation system 100 of FIG. 1 tensioned through bony structure 902, in accordance with one embodiment of the present disclosure. As depicted in FIG. 9, a first wire 104a and a second wire 104b are implanted into the subject's body and through soft tissue and bony structure 902. In order to tension the wires 104a, 104b to a desired tension, each wire is anchored to the external fixator frame 102 at first anchor locations proximate to each other and on the same side of the external fixator frame 102. In an embodiment, the first and second wires 104a, 104b are anchored at first anchor locations on the entry side of the subject's limb proximate to stoppers (not shown) on each wire that are in contact with the first cortex of the bony structure 902.

The first and second wires 104a, 104b may be received through first and second wire apertures 414a, 414b in first and second wire fixation bolts 106a, 106b, respectively. The first and second wire fixation bolts 106a, 106b may be inserted into bolt apertures 206 of the external fixator frame 102 proximate to the original orientation of the first and second wires 104a, 104b. First and second nuts 108a, 108b may then be threaded along the threaded shaft portions 404a, 404b such that the first and second nuts 108a, 108b bias the head portions of the first and second wire fixation bolts 106a, 106b against the upper surface 202 of the external fixator frame 102, thereby anchoring the first anchor locations for the first and second wires 104a, 104b. The first and second wires 104a, 104b may be anchored at the first anchor locations at separate times using only two tools—a first wrench to tighten the first nut 108a and a second wrench to provide counter torque against the first wire fixation bolt 106a to anchor the first wire 104a and then the same first wrench to tighten the second nut 108b and the same second wrench to provide counter torque against the second wire fixation bolt 106b to anchor the second wire 104b. Therefore, only one medical professional is needed to anchor the first and second wires 104a, 104b at their respective first anchor locations.

After the first and second wires 104a, 104b are anchored at their respective first anchor locations, the sharp tip ends of the first and second wires 104a, 104b proximate to the exit side of the subject's limb may be placed proximate to the external fixator frame 102. Depending on the desired orientation of the first and second wires 104a, 104b relative to the external fixator frame 102, the first wire 104a may be received through a wire aperture or an offset wire groove of a third wire fixation bolt 106c and the second wire 104b may be received through a wire aperture or an offset wire groove of a fourth wire fixation bolt 106d. Based on the configuration of apertures 206 in the external fixator frame 102, the surgeon may select either the wire apertures or offset wire groove of the third and fourth wire fixation bolts 106c, 106d. Preferably, the first and second wires 104a, 104b are placed in the wire apertures 414c, 414d of wire fixation bolts 106c, 106d, respectively, since this will maximizing the surface area contact of the wire fixation bolts 106c, 106d against the first and second wires 104a, 104b. This will increase the purchase of the wire fixation bolts 106c, 106d against the first and second wires 104a, 104b, thereby securing the degree of wire tension for a longer period of time. During the surgical application of this device, it may not always be possible to align the first and second wires 104a, 104b with the wire apertures 414c, 414d on the second anchor locations. As a result, the first and second wires 104a, 104b may be inserted into the offset wire grooves 416 of the first and second wire fixation bolts 106c, 106d to allow the first and second wire fixation bolts 106c, 106d to secure the first and second wires 104a, 104b for tensioning while minimizing the amount of bending of the wires. Once selected, the surgeon may then insert the third and fourth threaded shaft portions 404b, 404d of the third and fourth wire fixation bolts 106c, 106d, respectively, through bolt apertures 206 of the external fixator frame 102. The third and fourth threaded shaft portions 404c, 404d may be inserted into bolt apertures 206 of the external fixator frame 102 proximate to the original orientation of wires 104a, 104b. As shown in FIG. 9, the wire fixation bolts 106a, 106c may be inserted through a different side of the external fixator frame 102 than the wire fixation bolts 106b, 106d so as to provide spacing between the first and second wires 104a, 104b as the pass through the cortex of the bony structure 902.

After the third and fourth wire fixation bolts 106c, 106d are inserted into the external fixator frame 102, the first and second wires 104a, 104b may be received within first and second wire tensioners (not shown), respectively. The wire tensioning tip of the first wire tensioner may engage with the third wire fixation bolt 106c such that the first wire 104a and the third wire fixation bolt 106c cannot rotate. The wire tensioning tip of the second wire tensioner may engage with the fourth wire fixation bolt 106d such that the second wire 104b and the fourth wire fixation bolt 106d cannot rotate. Once both the first and second wire tensioners are engaged with the third and fourth wire fixation bolts 106c, 106d, the first and second wires 104a, 104b may be tensioned at the same time to a desired tension, e.g. 130 kilograms of tension for a 1.8 mm wire. The first and second wires 104a, 104b may tensioned at the same time using only two tools—the first wire tensioner and the second wire tensioner. Therefore, only one medical professional is needed to tension the first and second wires 104a, 104b. The operations of the wire tensioner 110 are described with reference to FIG. 13.

After the first and second wires 104a, 104b are tensioned to a desired tension, third and fourth nuts 108c, 108d may then be threaded along the third and fourth threaded shaft portions 404c, 404d such that the third and fourth nuts bias the head portions of the third and fourth wire fixation bolts 106c, 106d against the upper surface 202 of the external fixator frame 102, anchoring the second anchor locations for the first and second wires 104a, 104b. The first and second wires 104a, 104b may be anchored at the second anchor locations at separate times using only two tools at a time—a first wrench to tighten the third nut 108c and the first wire tensioner to provide counter torque against the third wire fixation bolt 106c to anchor the first wire 104a across the external fixator frame 102 with tension, and then the same first wrench to tighten the fourth nut 108d and the second wire tensioner to provide counter torque against the fourth wire fixation bolt 106d to anchor the second wire 104b across the external fixator frame 102 with tension. Therefore, only one medical professional is needed to anchor the first and second wires 104a, 104b at their respective second anchor locations.

As depicted in FIG. 9, an intersection angle Θ between the first and second wires 104a, 104b is preferably in the range of about 30° to about 60°. However, in an embodiment, an intersection angle Θ between the first and second wires 104a, 104b of approximately 45° may be utilized. If the first and second wires 104a, 104b are not tensioned at the same time with first and second wire tensioners, tensioning the second wire 104b may loosen or tighten the tension in the first wire 104a, thereby disfiguring the external fixator frame 102 and/or causing the first or second wires 104a, 104b to not be tensioned to the desired tension when anchored. For example, if the intersection angle Θ is less than 45°, if the first wire 104a is tensioned to a desired tension and then the second wire 104b is tensioned to a desired tension, the tension in the first wire 104a would be loosened and the first wire 104a would be under-tensioned. Conversely, if the intersection angle Θ is greater than 45°, if the first wire 104a is tensioned to a desired tension and then the second wire 104b is tensioned to a desired tension, the tension in the first wire 104a would be tightened and the first wire 104a would be over-tensioned. By placing the first and second wires 104a, 104b at an intersection angle Θ of approximately 45° and tensioning the first and second wires 104a, 104b at the same time, interference of the tensioning forces can be minimized.

Figure 10:
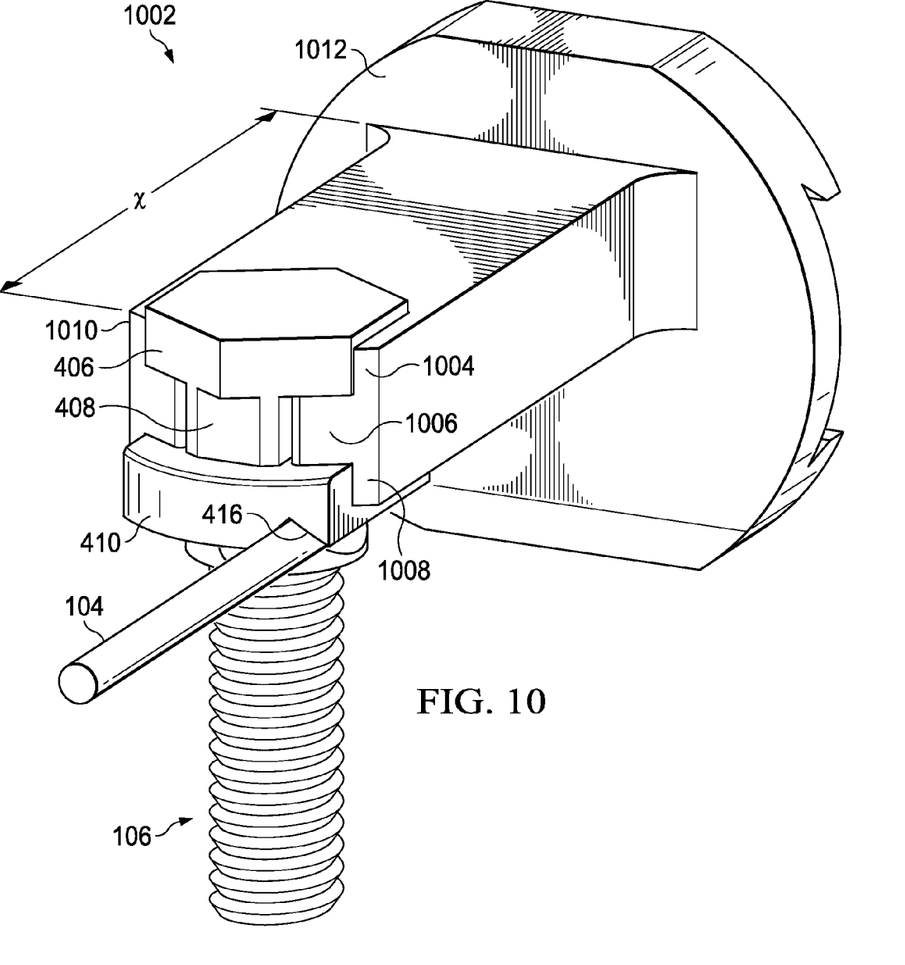
FIG. 10 illustrates an elevational view of a wire tensioning tip, in accordance with one embodiment of the present disclosure.

FIG. 10 illustrates an elevational view of a wire tensioning tip 1002, in accordance with one embodiment of the present disclosure. Like the wire tensioning tip 112 depicted in FIGS. 6-8, the wire tensioning tip 1002 may comprise a shaped head recess portion 1004 operable to engage with a shaped head 406 of a wire fixation bolt 106, a body shoulder portion 1006 distal to the shaped head recess portion 1004 and operable to engage with a first body 408, and a shoulder recess portion 1008 distal to the body shoulder portion 1006 and operable to engage with a shoulder portion 410 of a wire fixation bolt 106. The wire tensioning tip 1002 may engage with an entirety of four sides of a hex-shaped wire fixation bolt to releasably connect the wire tensioning tip 112 to the wire fixation bolt 106 and prevent it from rotating, twisting, and/or leaving the plane formed along the longitudinal axis of the wire 104 and the wire tensioning tip 1002, when a wire is tensioned. In FIG. 10, the wire 104 is depicted as being engaged with the offset wire groove 416 of the wire fixation bolt 106 rather than engaged with the wire fixation aperture (not shown). A distal end 1010 of the wire tensioning tip 1002 can be placed a distance $\chi$ from a base 1012 of the wire tensioning tip 1002. By doing this, the bending of the wire 104 arising from the lateral displacement can be minimized. Preferably, the distance $\chi$ should be in a range of approximately 30 to 50 mm.

Figure 11:
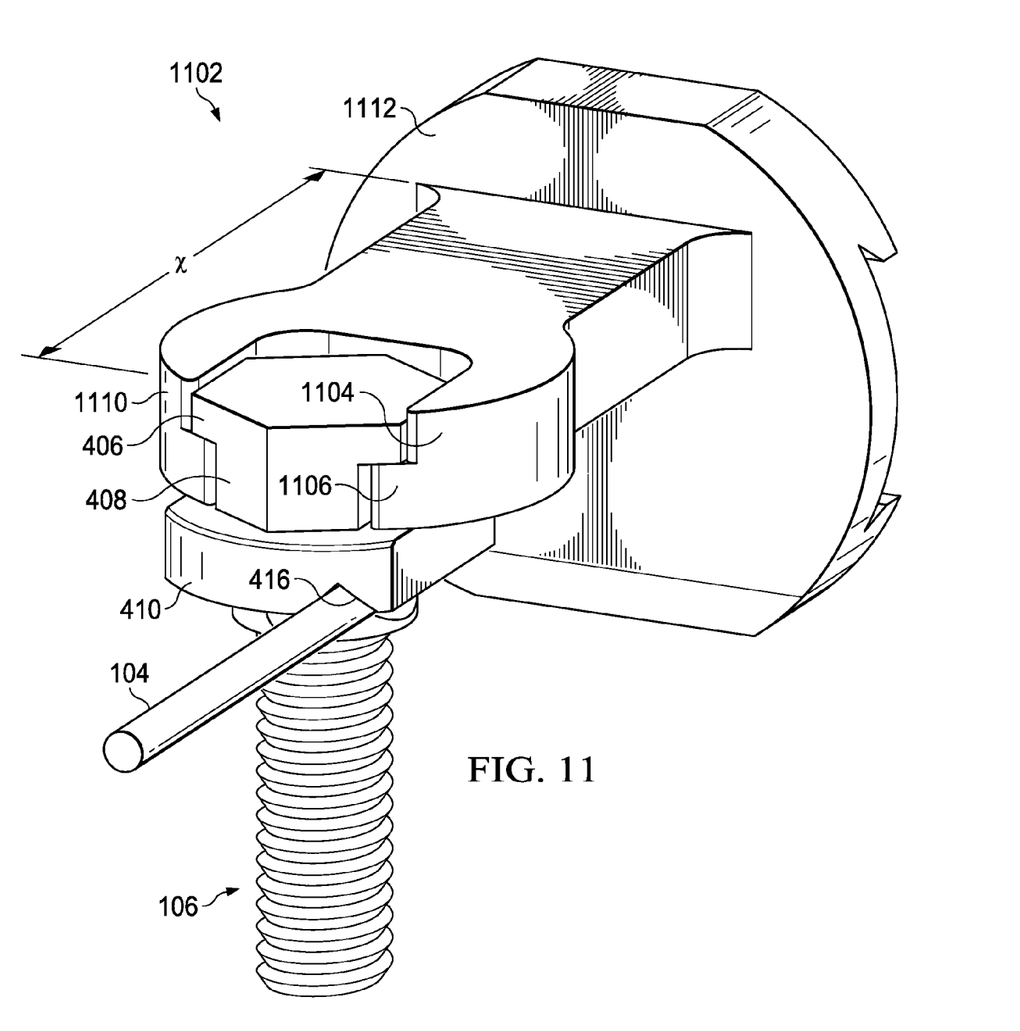
FIG. 11 illustrates an elevational view of a wire tensioning tip, in accordance with one embodiment of the present disclosure.

FIG. 11 illustrates an elevational view of a wire tensioning tip 1102, in accordance with one embodiment of the present disclosure. The wire tensioning tip 1102 may comprise a shaped head recess portion 1104 operable to engage with a shaped head 406 of a wire fixation bolt 106 and a body shoulder portion 1106 distal to the shaped head recess portion 1104 and operable to engage with a first body 408 of a wire fixation bolt 106. The wire tensioning tip 1102 may engage with an entirety of four sides of a hex-shaped wire fixation bolt to releasably connect the wire tensioning tip 1102 to the wire fixation bolt 106 to prevent it from rotating, twisting, and/or leaving the plane formed along the longitudinal axis of the wire 104 and the wire tensioning tip 1102 when a wire is tensioned. In FIG. 11, the wire 104 is depicted as being engaged with the offset wire groove 416 of the wire fixation bolt 106 rather than engaged with the wire fixation aperture (not shown). Much like the embodiment of FIG. 10, a distal end 1110 of the wire tensioning tip 1102 can be placed a distance $\chi$ from a base 1112 of the wire tensioning tip 1102.

Figure 12:
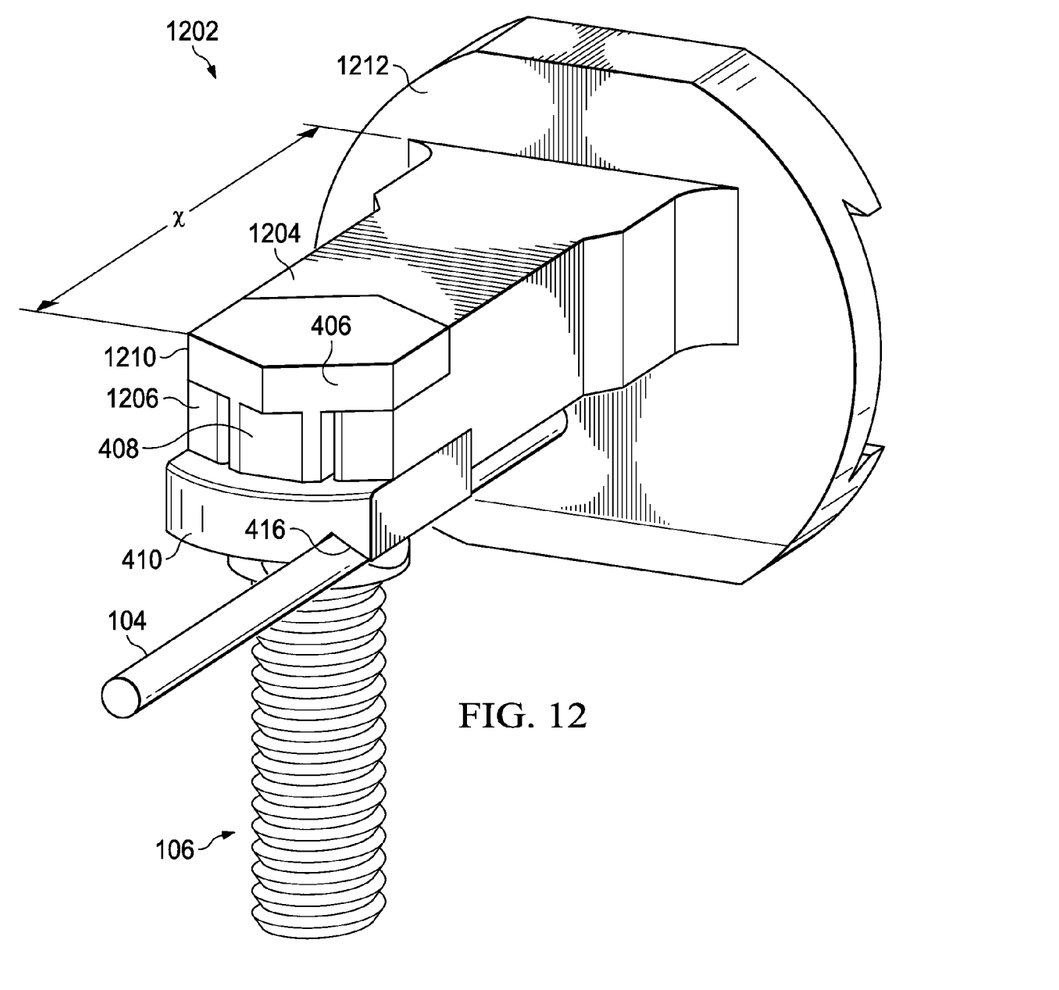
FIG. 12 illustrates an elevational view of a wire tensioning tip, in accordance with one embodiment of the present disclosure.

FIG. 12 illustrates an elevational view of a wire tensioning tip 1202, in accordance with one embodiment of the present disclosure. The wire tensioning tip 1202 may comprise a shaped head portion 1204 operable to engage with a shaped head 406 of a wire fixation bolt 106 and a body shoulder portion 1206 distal to the shaped head portion 1204 and operable to engage with a first body 408 of a wire fixation bolt 106. The wire tensioning tip 1202 may engage with two sides of a hex-shaped wire fixation bolt to releasably connect the wire tensioning tip 1102 to the wire fixation bolt 106 and prevent it from rotating, twisting, and/or leaving the plane formed along the longitudinal axis of the wire 104 and the wire tensioning tip 1202 when a wire is tensioned. In FIG. 12, the wire 104 is depicted as being engaged with the offset wire groove 416 of the wire fixation bolt 106 rather than engaged with the wire fixation aperture (not shown). Much like the embodiments of FIG. 10 and FIG. 11, a distal end 1210 of the wire tensioning tip 1202 can be placed a distance $\chi$ from a base 1212 of the wire tensioning tip 1202.

FIG. 13 illustrates the tensioner device 110 with the wire tensioning tip 112 of FIG. 1, in accordance with one embodiment of the present disclosure. As previously discussed, the wire tensioning tip 112 of the present disclosure may be connected to and extend from any known wire tensioner 110, such as the Orthofix TrueLok® wire tensioner.

In each of the embodiments depicted in FIGS. 1-13, the first and second wires may be tensioned across either the upper or lower surfaces of the external fixator frame depending on the desired placement of the first and second wires through the subject's limb. In embodiments, both wires may be tensioned across the upper surface of the external fixator frame, both wires may be tensioned across the lower surface of the external fixator frame, or one way may be tensioned across the upper surface of the external fixator frame and one wire tensioned across the lower surface of the external fixator frame. In addition, the wire fixation bolts may be used with one or more spacers or washers in order to space the wire apertures or the offset wire grooves of the wire fixation bolts further from the upper or lower surfaces of the external fixator frame in order to achieve the desired orientation and tension within first and second wires across the external fixator frame. In embodiments, more than two wires may be tensioned across the external fixator frame and more than one external fixator frame may be received onto the subject's limb.

In each embodiment, the wire tensioning tips engage the wire fixator bolts instead of the external fixator frame, which advantageously allows the first and second wires to be placed at an orientation angles across the external fixator frame that are not orthogonal to the external fixator frame. By having the wire tensioning tips engage the wire fixator bolts instead of the external fixator frame, irregularly shaped external fixator frames may be used without fear of the wire tensioners slipping against the external fixator frame. In addition, by engaging the wire fixator bolts with the wire tensioning tips, fewer tools are needed and one medical professional can tension to the desired tension and anchor both wires across the external fixator frame, if desired.

One or more components of the improved wire fixation systems disclosed herein may be made from any of the following materials: (a) any biocompatible material (which biocompatible material may be treated to permit bone ingrowth or prohibit bone ingrowth); (b) a plastic; (c) a fiber; (d) a polymer; (e) a metal (e.g., a pure metal such as titanium and/or an alloy such as Ti—Al—Nb, TI-6Al-4V, stainless steel); (f) a radiolucent material (e.g., carbon fiber, PEEK or aluminum); or (g) any combination thereof.

While various embodiments in accordance with the principles disclosed herein have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

It will be understood that the principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language under this heading to describe the so-called technical field. Further, a description of technology in the "Background" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

What is claimed is:

1. A wire fixation system comprising:
   an external fixator frame comprising an upper surface and a lower surface and a plurality of bolt apertures extending from the upper surface to the lower surface;
   a wire operable to be extended across the external fixator frame and through a bony structure;
   at least first and second wire fixation bolts extending along an axis and operable to be received through a bolt aperture of the external fixator frame, each wire fixation bolt comprising:
      a head portion, wherein the head portion further comprises:
         a shaped head;
         a first body distal to the shaped head;
         a shoulder distal to the first body;
         a second body distal to the shoulder;
         a wire aperture extending perpendicularly to the axis of the wire fixation bolt and through the second body; and
         an offset wire groove extending perpendicularly to the axis of the wire fixation bolt and partially through a distal surface of the shoulder and partially though a proximal portion of the second body; and
      a threaded shaft portion;
   at least first and second nuts operable to be threaded onto the threaded shaft portions of the at least first and second wire fixation bolts, wherein the nuts are operable to bias the head portions of the wire fixation bolts against the upper surface of the external fixator frame; and
   a wire tensioning tip operable to engage with at least the second wire fixation bolt and with a wire tensioning device, the tensioning tip further comprising:
      a shaped head recess portion operable to engage with the shaped head of the wire fixation bolt; and
      a body shoulder portion distal to the shaped head recess portion and operable to engage with the first body of the wire fixation bolt;
   wherein the wire tensioning tip is operable to stabilize the head portion of the second wire fixation bolt and prevent the second wire fixation bolt from rotating when the wire tensioning tip is received onto the wire and engaged with the shaped head of the second wire fixation bolt;
   wherein the shaped head of the first and second wire fixation bolts and the shaped head portion of the wire tensioning tip are multi-faceted; and
   wherein the wire tensioning tip further comprises a shoulder recess portion distal to the body shoulder portion and operable to engage with the shoulder of the wire fixation bolt.

2. The wire fixation system of claim 1, wherein a first end of the wire may be secured to the external fixator frame with the first wire fixation bolt and the first nut.

3. The wire fixation system of claim 2, wherein the first end of the wire may be received through the wire aperture of the head portion of the first wire fixation bolt and anchored between the head portion of the first wire fixation bolt and the upper surface of the external fixator frame.

4. The wire fixation system of claim 1, wherein a second end of the wire may be secured to the external fixator fame with the second wire fixation bolt and the second nut.

5. The wire fixation system of claim 4, wherein the second end of the wire may be received through the wire aperture of the head portion of the second wire fixation bolt and anchored between the head portion of the second wire fixation bolt and the upper surface of the external fixator frame.

6. The wire fixation system of claim 4, wherein the second end of the wire may be received through the offset wire groove of the head portion of the second wire fixation bolt and anchored between the head portion of the second wire fixation bolt and the upper surface of the external fixator frame.

7. The wire fixation system of claim 1, wherein the shaped head of the first and second wire fixation bolts and the shaped head portion of the wire tensioning tip are hex-shaped.

8. The wire fixation system of claim 1, wherein the shaped head of the first and second wire fixation bolts and the shaped head portion of the wire tensioning tip are rounded.

9. The wire fixation system of claim 1, wherein the wire tensioner is operable to tension the wire against the wire fixation bolt to approximately 130 kilograms while preventing the second wire fixation bolt from rotating.

10. The wire fixation system of claim 1, wherein the second nut is operable tighten the second wire fixation bolt against the lower surface of the external fixation frame while the wire tensioning tip is engaged with and preventing the second wire fixation bolt from rotating.

11. The wire fixation system of claim 1, wherein a first wire is anchored by the first and second fixation bolts and tensioned by a first wire tensioner and wire tensioner tip.

12. The wire fixation system of claim 11, wherein a second wire is anchored by third and fourth wire fixation bolts and tensioned by a second wire tensioner and wire tensioner tip.

13. The wire fixation system of claim 12, wherein the first and second wire tensioners and wire tensioner tips tension the first and second wires across the external fixator frame at the same time.

14. The wire fixation system of claim 1, wherein the wire tensioning tip further comprises:
a boss attached to an underside of the wire tensioning tip, wherein the boss allows the wire tensioning tip to align with a portion of the wire fixation bolt.

15. The wire fixation system of claim 14, wherein the boss has the same height as the difference in the height between the wire aperture and the offset wire groove of the head portion of the wire fixation bolt, thus allowing the wire tensioning tip to align with the wire aperture when the wire tensioning tip engages with the wire fixation bolt.

16. The wire fixation system of claim 14, wherein the boss has the same height as the difference in the height between the wire aperture and the offset wire groove of the head portion of the wire fixation bolt, thus allowing the wire tensioning tip to align with the offset wire groove when the wire tensioning tip engages with the wire fixation bolt.

17. The wire fixation system of claim 14, wherein a distal end of the wire tensioning tip and a base of the wire tensioning tip are spaced at a distance $\chi$ calculated to minimize the bending of the wire due to lateral displacement.

18. A wire tensioning tip and wire tensioning bolt system comprising:
at least one wire fixation bolt extending along an axis, the wire fixation bolt comprising:
a head portion, wherein the head portion further comprises:
a shaped head;
a first body distal to the shaped head;
a shoulder distal to the first body;
a second body distal to the shoulder;
a wire aperture extending perpendicularly to the axis of the wire fixation bolt and through the second body; and
an offset wire groove extending perpendicularly to the axis of the wire fixation bolt and partially through a distal surface of the shoulder and partially though a proximal portion of the second body; and
a threaded shaft portion; and
a wire tensioning tip operable to engage with the wire fixation bolt and with a wire tensioning device, the tensioning tip further comprising:
a shaped head recess portion operable to engage with the shaped head of the wire fixation bolt; and
a body shoulder portion distal to the shaped head recess portion and operable to engage with the first body of the wire fixation bolt;
wherein the wire tensioning tip is operable to stabilize the head portion of the wire fixation bolt and prevent the wire fixation bolt from rotating when the wire tensioning tip is received onto a wire and engaged with the shaped head of the wire fixation bolt;
wherein the shaped head of the wire fixation bolt and the shaped head portion of the wire tensioning tip are multi-faceted; and
wherein the wire tensioning tip further comprises a shoulder recess portion distal to the body shoulder portion and operable to engage with the shoulder of the wire fixation bolt.

19. The wire tensioning tip and wire tensioning bolt system of claim 18, wherein the wire may be received through the wire aperture of the head portion of the wire fixation bolt and is operable to be anchored between the head portion of the wire fixation bolt and an upper surface of an external fixator frame.

20. The wire tensioning tip and wire tensioning bolt system of claim 18, wherein the wire may be received through the offset wire groove of the head portion of the wire fixation bolt and is operable to be anchored between the head portion of the wire fixation bolt and an upper surface of an external fixator frame.

21. The wire tensioning tip and wire tensioning bolt system of claim 18, wherein the shaped head of the wire fixation bolt and the shaped head portion of the wire tensioning tip are hex-shaped.

22. The wire tensioning tip and wire tensioning bolt system of claim 18, wherein the shaped head of the wire fixation bolt and the shaped head portion of the wire tensioning tip are rounded.

23. The wire tensioning tip and wire tensioning bolt system of claim 18, wherein the wire tensioner is operable to tension the wire against the wire fixation bolt to approximately 130 kilograms while preventing the wire fixation bolt from rotating.

24. A method for tensioning a wire across an external fixation element, the method comprising:
providing an external fixator frame comprising an upper surface and a lower surface and at least one bolt aperture extending from the upper surface to the lower surface;
providing first and second wire fixation bolts extending along an axis, each wire fixation bolt comprising:
a head portion, wherein the head portion further comprises:
a shaped head;
a first body distal to the head;

a shoulder distal to the first body;
a second body distal to the shoulder;
a wire aperture extending perpendicularly to the axis of the wire fixation bolt and through the second body; and
an offset wire groove extending perpendicularly to the axis of the wire fixation bolt and partially through a distal surface of the shoulder and partially though a proximal portion of the second body; and
a threaded shaft portion;
providing first and second nuts operable to be threaded onto the threaded shaft portions of the first and second wire fixation bolts;
securing a first end of a wire between the first wire fixation bolt and the upper surface of the external fixator frame by inserting the wire through the wire aperture of the first wire fixation bolt, inserting the threaded portion of the first wire fixation bolt through a first aperture of the external fixator frame, and rotating the first nut about the threaded portion of the first wire fixation bolt, thereby biasing the head portion of the first wire fixation bolt against the upper surface of the external fixator frame;
providing a wire tensioning tip operable to engage with the second wire fixation bolt and with a wire tensioning device, the tensioning tip further comprising:
a shaped head recess portion operable to engage with the shaped head of the wire fixation bolt; and
a body shoulder portion distal to the shaped head recess portion and operable to engage with the first body of the wire fixation bolt;
securing a second end of the wire between the first wire fixation bolt and the upper surface of the external fixator frame by inserting the wire through the wire aperture or the offset wire groove of the second wire fixation bolt, inserting the threaded portion of the second wire fixation bolt through a second aperture of the external fixator frame, receiving the tensioner over the wire proximate to the second end of the wire, engaging the wire tensioning tip with the head portion of the second wire fixation bolt, tensioning the wire across the external fixation frame, and rotating the second nut about the threaded portion of the second wire fixation bolt, thereby biasing the head portion of the second wire fixation bolt against the upper surface of the external fixator frame;
wherein the wire tensioning tip is operable to stabilize the head portion of the second wire fixation bolt and prevent the second wire fixation bolt from rotating when the wire tensioning tip is received onto the wire and engaged with the shaped head of the second wire fixation bolt;
wherein the shaped head of the wire fixation bolt and the shaped head portion of the wire tensioning tip are multi-faceted; and
wherein the wire tensioning tip further comprises a shoulder recess portion distal to the body shoulder portion and operable to engage with the shoulder of the wire fixation bolt.

25. The method of claim 24, wherein the wire is received and tensioned through a bony structure.

26. The method of claim 24, wherein the shaped distal head of the first and second wire fixation bolts and the shaped head portion of the wire tensioning tip are hex-shaped.

27. The method of claim 24, wherein the shaped distal head of the first and second wire fixation bolts and the shaped head portion of the wire tensioning tip are rounded.

28. The method of claim 24, wherein the wire tensioner is operable to tension the wire against the second wire fixation bolt to approximately 130 kilograms while preventing the second wire fixation bolt from rotating.

29. A wire fixation bolt comprising:
a head portion, wherein the head portion further comprises:
a multi-faceted head;
a first body distal to the multi-faceted head;
a shoulder distal to the first body;
a second body distal to the shoulder;
a wire aperture extending perpendicularly to the axis of the wire fixation bolt and through the second body; and
an offset wire groove extending perpendicularly to the axis of the wire fixation bolt and partially through a distal surface of the shoulder and partially though a proximal portion of the second body; and
a threaded shaft portion;
wherein the multi-faceted head and the shoulder have a first diameter and the first body has a second, smaller diameter;
wherein an outer surface of the multi-faceted head is operable to engage a first surface of a tensioning device;
wherein a lower surface of a distal portion of the multi-faceted head is operable to engage a second surface of the tensioning device, the lower surface being distal to the outer surface and perpendicular to the outer surface; and
wherein an outer surface of the first body is operable to engage an inner surface of the tensioning device.

* * * * *